United States Patent [19]

Fiebig et al.

[11] 4,396,717

[45] Aug. 2, 1983

[54] NUTRIENT MEDIUM CARRIER SYSTEM

[75] Inventors: Reinhard Fiebig, Idstein; Hans Schleussner, Frankfurt, both of Fed. Rep. of Germany

[73] Assignee: Biotest-Serum-Institut GmbH, Frankfurt am Main, Fed. Rep. of Germany

[21] Appl. No.: 285,647

[22] Filed: Jul. 21, 1981

[30] Foreign Application Priority Data

Jul. 25, 1980 [DE] Fed. Rep. of Germany ....... 3028204

[51] Int. Cl.³ .................. C12M 3/00; C12M 1/20; C12M 1/18
[52] U.S. Cl. ................................. 435/301; 435/300; 435/61; 435/45.19
[58] Field of Search .............. 435/301, 300, 299, 810; 422/61; 206/45.19; 220/21, 346, 351

[56] References Cited

U.S. PATENT DOCUMENTS

| 601,568 | 3/1898 | Jacoby | 220/346 X |
|---|---|---|---|
| 2,472,582 | 6/1949 | Green | 220/346 |
| 3,563,859 | 2/1971 | Fink | 435/301 X |
| 3,726,767 | 4/1973 | White | 435/301 X |
| 3,883,398 | 5/1975 | Ono | 435/301 X |
| 4,113,098 | 9/1978 | Howard | 220/351 X |
| 4,299,920 | 11/1981 | Peters | 435/301 X |

FOREIGN PATENT DOCUMENTS 444726 of 1926 Australia ............................. 220/351

Primary Examiner—Kenneth M. Schor
Attorney, Agent, or Firm—Sprung, Horn, Kramer & Woods

[57] ABSTRACT

A nutrient medium carrier system comprising a sterilizable plastic nutrient medium carrier, a sterilizable plastic cover, and a sealing foil, the nutrient medium carrier having a depression to receive the nutrient medium, a surrounding beaded edge above the surface of the nutrient medium, a handle on one end, and a flat edge running around both sides and the other end, the depression being subdivided into compartments by means of ridges; the cover having a depression and a surrounding flat edge to receive the sealing foil, the cover depression gradually widening on two sides and one end to a flat edge up to the dimensions of the nutrient medium carrier, the narrow part being of such size that both side walls and one end touch the beaded edge on two sides and on the end opposite the handle, the cover having a steplike offset with locking flanges on its upper edge to hold the nutrient medium carrier, the flat edge of the carrier contacting the steplike offset of the cover, the cover on the side on which the handle of the nutrient medium carrier comes to lie being rounded off or slanted and provided with a hollow for gripping and pulling out the nutrient medium carrier from the cover.

12 Claims, 3 Drawing Figures

NUTRIENT MEDIUM CARRIER SYSTEM

BACKGROUND OF THE INVENTION

The present invention relates to a nutrient medium carrier system consisting of a nutrient medium carrier, a covering, and a sealing foil.

Nutrient medium carriers filled with a nutrient medium serve the purpose of culturing microorganisms and of determining microorganisms, i.e. ascertaining their presence and quantity.

For inoculation with microorganisms, so called Petri dishes have been used until now. The bottoms of these are covered with a layer of a nutrient medium, and they may be either round or rectangular. The bottoms may be plain or partitioned. These dishes are closed with a cover that can be put on top of them (cf. Greiner, *Labortechnik fur Medizin und Forschung*, 1976: 35–36).

Surface contact cultures or so-called dip slides serve for the identification of localized microorganisms. Until now contact dishes were used for surface contact cultures. These are shaped like Petri dishes, buty they have a lower edge, above which the nutrient medium projects.

The so-called dip slides are strips coated with a nutrient medium, which are selaed up in a little tube with a stopper or similar seal that cannot be penetrated by microorganisms, and which can be used for determining microorganisms in liquid media.

A device for testing the air for its microorganism content is known, moreover, from German Pat. No. 2,301,385, and in this device a carrier foil that is coated with a nutrient medium is used, which corresponds in length to the width of the device, and which is divided up into cups to receive the nutrient medium.

Both Petri dishes and contact dishes and dip slides are relatively expensive, and at the same time, both types of dishes, moreover, involve a high risk of contamination, especially during shipping, too, since they can not be tightly sealed before use.

Beyond this, each of the three types of container requires separate handling, separate instruments, etc., and the user who is concerned with all three types of determining microorganisms needs to keep a separate inventory of each of these containers.

Petri dishes have been used essentially unchanged, for microbiological tests, practically since the time of Robert Koch, that is, for about 100 years. The only change is that plastic is used today as the material for the dishes, as well as the glass that was originally used. The Petri dish system could be looked upon as somewhat satisfactory and useful as long as it was mainly applied for the needs of a small group of users and the tests were carried out on a small scale.

With increasing technology and rationalizing, the need arose for a system that is easier and more economical with regard to manufacturing, provides standardized quality, and is protected from secondary contamination.

The foil described in German Pat. No. 2,301,385, to be sure, also has sterile packaging, but after the sealing foil has been removed, and after use for testing the air for its microorganism content, the nutrient medium carrier can no longer be automatically affixed to the covering. The system can only be sealed with the aid of an adhesive strip, or a slide, or similar measures. Besides, the foil is fashioned in such a way that it can be specially used only in the device intended for it.

It was the objective of the present invention, therefore, to manufacture a hermetically sealed, multi-purpose container that could not be penetrated by microorganisms, which ought not only to replace the Petri dish, but can also be used for surface contact cultures and determining microorganisms in fluids, which can be made economically in a rational manner, the seal of which can not be penetrated by microorganisms even during shipment, and which can be adequately sealed again after inoculation until incubation.

SUMMARY OF THE INVENTION

According to the present invention, this problem is solved by means of a nutrient medium carrier system of a nutrient medium carrier (1), cover (2), and sealing foil (3), characterized in that the nutrient medium carrier (1) has a depression (4) intended to receive the nutrient medium, is subdivided by ridges (5) into compartments (6), has a surrounding beaded edge (7) raised up from the surface of the nutrient medium, a handle (8) at one end, a flat edge (9) running around both sides and the other end. The cover (2) has a depression (10) and a surrounding flat edge (11) to receive the sealing foil (3), and at the same time, the depression (10) gradually widens on two sides and one end to the flat edge (11) up to the dimensions of the nutrient medium carrier (1). The narrower part is measured in such a way that both side walls and one end touch the beaded edge (7) on two sides and on the end opposite the handle (8).

The steplike offset (12) has locking flanges (13) on its upper edge that hold the nutrient medium carrier (1) fast, the flat edge (9) of which rests on the steplike offset, and the depression (19) on the side on which the handle (8) of the nutrient medium carrier (1) comes to lie is rounded off or slanted, and the rounded or slanted part is provided with a hollow (14) for gripping and pulling out the nutrient medium carrier (1), with the nutrient medium carrier (1) and the cover (2) consisting of plastic foil that can be sterilized.

The nutrient medium carrier, the cover, and the sealing foil consist of a foil that can be sterilized, and at the same time, the first two can be manufactured in a way that is technologically simple, with the aid of deep-drawing equipment. It is preferable to use thermoplastic material, such as, for example, PVC, polyester, polystyrene, polyethylene, and polypropylene as a plastic that can be sterilized.

The nutrient medium carrier is coated with nutrient medium, inserted into the cover with the coated side down, and hermetically sealed with the sealing foil by sealing the foil down airtight onto the flat edge of the cover. For special purposes, however, the system of nutrient medium carrier, cover, and sealing foil can, first of all, be manufactured, sterilized, and sold even without the nutrient medium.

It is preferable for the nutrient medium carrier to have a rectangular shape, and it is especially preferable for it to have the dimentions 100×50 mm. It may, of course, also be larger or smaller.

It is preferable for the depression in the nutrient medium to have an area of 25 cm$^2$, which permits a simple conversion to the standard expression of microorganisms per m$^2$ of area. This area is partitioned into compartments that are grooved, with the result that the nutrient medium is held in place more firmly and the counting of the microorganisms is facilitated. It is preferable for the compartments to be square or rectangular and to have an area of 1 cm$^2$, with the separation of the compartments being effected by means of cross-ridges and longitudinal ridges. For stabilizing, it is preferable, with a rectangular nutrient medium carrier, for the cross-ridges to be somewhat higher than the longitudinal ridges.

The beaded edge surrounding the nutrient medium surface may vary in height, depending on the intended use. With a high edge and a nutrient medium level below the edge, the system can be used as a so-called "petri dish," while with a low edge, with which the nutrient medium level arches out over the edge, the system may be used for the determination of microorganisms on surfaces or in fluids; that is, as a contact plate, microorganism indicator, dip slide, etc.

In addition, the system can be used for the determination of microbiological sensitivity (resistance to antibiotics) and the identification of causative organisms (variegated series).

In the form of construction with a high edge, it is preferable to have the height of the edge 8 mm, while with the low form of construction, it is preferable for the height of the edge to be 4 mm. Both forms of construction can be manufactured with the very same forming tool; the height of its edge just has to be adjusted. The form of construction with the low edge may expediently be flexible, which presents a special advantage in its use as a contact plate.

With this form of construction, furthermore, it may be expedient to pass the beaded edge through the flat edge at one or more places, like a groove, in order to assure better drainage, for example, when it is used with liquids.

When the nutrient medium carrier is filled with nutrient medium, it is advantageous for the nutrient medium level to be about 2.5 mm below the edge.

In a special form of construction, the depression in the nutrient medium carrier may again be subdivided by one or more walls, and at the same time, various nutrient media may be introduced into the indivudal compartments.

The nutrient medium carrier has a handle at one end, so that it may be manipulated without touching the nutrient medium. The handle may be profiled for stability. It is suitable for the handle to extend across the width of the nutrient medium carrier, and it has a length of about 20 to 25 mm.

The cover consists of the depression and the flat edge together. The depression in which the nutrient medium carrier is placed gradually widens toward the flat edge up to the dimensions of the nutrient medium carrier, while the narrower bottom part is measured in such a way that both side walls and one end wall touch the beaded edge of the nutrient medium carrier—to be more precise, both side walls and the end wall opposite the handle. By "touch", it is meant that when the carrier is inserted into the cover, the walls slide together. The flat edge of the carrier that surrounds the beaded edge slides on the step. On the upper part of the step are the locking flanges that fix the nutrient medium carrier into place. As a result, after the removal of the sealing foil and after inoculation, the nutrient medium carrier can be inserted or snapped firmly into the cover, so that sterile manipulation up to incubation is assured.

These locking flanges may be attached at a distance from each other around the three sides of the cover; however, they may also be continuous.

The side of the cover that the handle of the carrier comes to rest on is rounded off or slanted, so that the carrier can not slide out. It is, furthermore, provided with a hollow of such a nature that one may stick one's fingers in, and easily grasp the nutrient medium carrier and pull it out. Besides, this hollow serves the required exchange of gases.

The same cover may be used for both types of nutrient medium carriers, that is, with the high and the low beaded edge. In each case, the dimension of the hollow must be of such a nature that a gap remains between the beaded edge of the carrier and the bottom of the cover for the exchange of gases. The width of this gap is optional; however, it is expedient for it to be about 1 to 4 mm.

The sealing foil, which seals the whole system hermetically and sterilely, is stuck onto the flat edge of the cover.

BRIEF DESCRIPTION OF THE DRAWINGS

The present invention is explained below in further detail with reference to the accompanying drawing wherein.

DETAILED DESCRIPTION OF THE INVENTION

Figure 1:
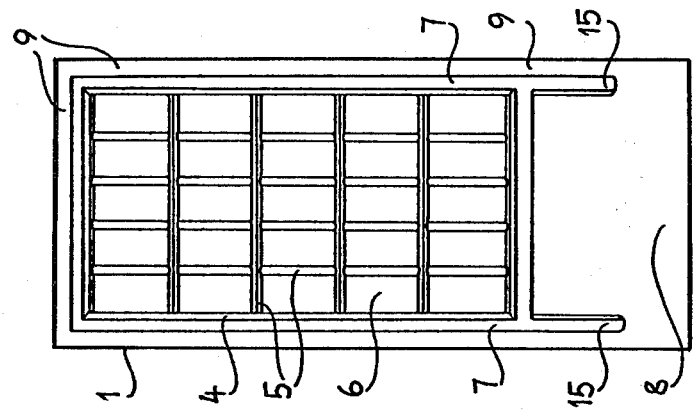
FIG. 1 shows a top view of the nutrient medium carrier.

The nutrient medium carrier (1) shown in FIG. 1 has a rectangular hollow (4) intended to receive the nutrient medium; it is subdivided into rectangular compartments (6) by means of ridges (5). A beaded edge (7) that is raised up from the bottom of this hollow runs around the whole hollow (4). At one end of the nutrient medium carrier, the handle (8) can be seen, which is reinforced by a stabilizing profile (15). In this form of construction, extensions of the beaded edge (7) represent the stabilizing profile (15). A flat edge (9), which lies in the same plane as the handle (8), runs around the whole arrangement.

Figure 2:
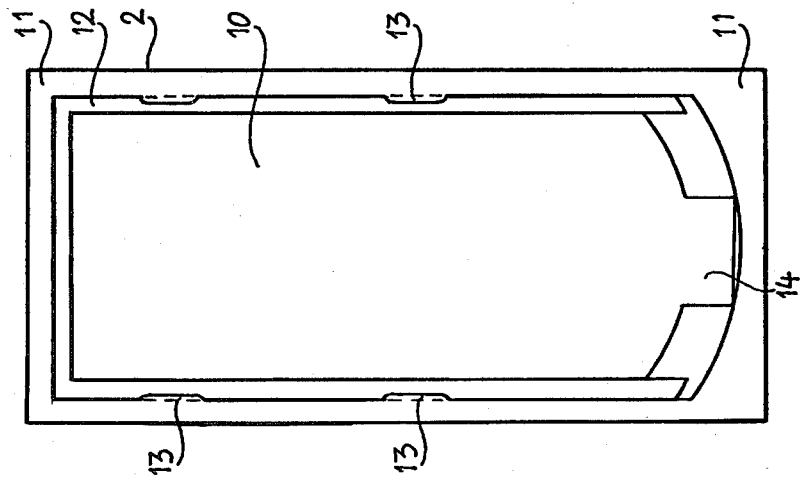
FIG. 2 shows a top view of the covering.

The cover (2) shown in FIG. 2 has a troughlike hollow (10), which has a rounding with a recess (14) at the end on which the handle of the nutrient medium carrier is supposed to come to rest. Around the three straight sides, runs a steplike offset (12), and around the whole arrangement, a flat edge (11) for applying a sealing foil that is supposed to hermetically seal the whole nutrient medium carrier system. Around the three straight sides, on the inside of the flat edge (11), are locking flanges (13), which serve to hold the nutrient medium carrier in place in the inserted state, even when the sealing foil has already been removed.

Figure 3:
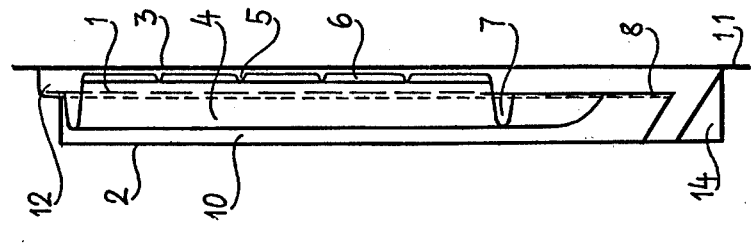
FIG. 3 shows a side view of a nutrient medium carrier system according to the present invention.

FIG. 3 shows the whole nutrient medium carrier system according to the present invention, in which the nutrient medium carrier (1) rests with the hollow (4) intended to receive the nutrient medium down, that is, pointing toward the bottom of the cover (2) and inserted into it. The whole article is sealed with sealing foil (3), which rests tight and flush on the flat edge (11) of the covering (2). In this vertical section, the steplike offset (12), the beaded edge (7), the troughlike hollow (4) in the nutrient medium carrier, as well as the ridges (5), which further subdivide this hollow into cuplike compartments (6) that receive and hold the nutrient medium in place can all be seen. The compartments may be filled with different types of nutrient medium. Furthermore, the position of the handle (8) in the hollow (10) of the cover (2) and the recess (14) into which one can reach and get hold of the handle can also be seen. In addition, the locking flanges (13) that form a kind of groove, by means of which the flat edge (9) of the nutrient medium carrier (1) and thus the whole nutrient medium carrier is held in place, can also be seen.

It will be appreciated that the instant specification and examples are set forth by way of illustration and not limitation, and that various modifications and changes may be made without departing from the spirit and scope of the present invention.

We claim:

1. A nutrient medium carrier system comprising together in combination
   (1) a sterilizable plastic nutrient medium carrier,
   (2) a sterilizable plastic cover, and
   (3) a sealing foil,
   the nutrient medium carrier having a portion thereof defining a depression to receive the nutrient medium, said depression surrounded by and defined by a wall, said depression having a base, a beaded edge adjacent the top of said wall and above said base defining a rim for said depression, a handle on one end of the carrier, and a flat edge extension of the handle running around the carrier, the depression being subdivided into compartments by means of ridges extending upwardly from the base;
   the cover having a portion defining a depression and a surrounding flat edge for receiving the sealing foil, the cover depression gradually widening on two sides and an end to the surrounding flat edge, to accommodate the dimensions of the nutrient medium carrier, the narrow part of the cover depression being of such size that said two sides and an end touch the beaded edge on the carrier's two sides and on the end opposite the handle, the cover having a steplike shelf-like offset adjacent and below the surrounding flat edge and adjacent the cover depression and the cover having locking flanges on its upper edge to hold the nutrient medium carrier, the flat edge of the carrier contacting the steplike offset of the cover with the locking flanges holding the carrier flat edge in place, the portion of the cover on the side on which the handle of the nutrient medium carrier comes to lie being rounded off or slanted and provided with a hollow to enable gripping and pulling out the nutrient medium carrier from the cover.

2. A nutrient medium carrier system according to claim 1, wherein the nutrient medium carrier and the cover have a rectangular shape.

3. A nutrient medium carrier system according to claim 1, wherein the nutrient medium carrier has the approximate dimensions 100×50 mm.

4. A nutrient medium carrier system according to claim 1, wherein the carrier depression which receives the nutrient medium has a surface of about 25 cm².

5. A nutrient medium carrier system according to claim 1, wherein the compartments have an area of about 1 cm².

6. A nutrient medium carrier system according to claim 1, wherein the compartments have a rectangular shape.

7. A nutrient medium carrier system according to claim 2, wherein the ridges are parallel to the carrier sides, the 50 mm ridges being higher than the 100 mm ridges.

8. A nutrient medium carrier system according to claim 1, wherein the handle is profiled for stability.

9. A nutrient medium carrier system according to claim 1, wherein the beaded edge has a height of about 4 mm.

10. A nutrient medium carrier system according to claim 1, wherein the beaded edge has a height of about 8 mm.

11. A nutrient medium carrier system according to claim 1, wherein the carrier depression is filled with nutrient medium.

12. A nutrient medium carrier system according to claim 1, wherein the compartments are filled with different types of nutrient medium.

* * * * *